United States Patent
de Troostembergh et al.

US006440712B2

(10) Patent No.: US 6,440,712 B2
(45) Date of Patent: Aug. 27, 2002

(54) PROCESS FOR PRODUCING AND RECOVERING ERYTHRITOL FROM CULTURE MEDIUM CONTAINING THE SAME

(75) Inventors: Jean-Claude Marie-Pierre Ghislain de Troostembergh, Houwaart; Ignace André Debonne, Vollezele; Willy Richard Obyn, Kampenhout, all of (BE)

(73) Assignee: Cerestar Holding B.V., Sas van Gent (NL)

( * ) Notice: Subject to any disclaimer, the term of this patent is extended or adjusted under 35 U.S.C. 154(b) by 0 days.

(21) Appl. No.: 09/731,858

(22) Filed: Dec. 8, 2000

(30) Foreign Application Priority Data

Dec. 10, 1999 (GB) ................................. 9929128

(51) Int. Cl.[7] .................................................. C12P 7/18
(52) U.S. Cl. ........................ 435/158; 435/171; 435/911
(58) Field of Search ................................. 435/158, 171, 435/911

(56) References Cited

U.S. PATENT DOCUMENTS

| | | | | |
|---|---|---|---|---|
| 4,906,569 A | | 3/1990 | Maeda et al. | 435/158 |
| 5,756,865 A | * | 5/1998 | Elseviers et al. | 568/864 |
| 5,902,739 A | * | 5/1999 | Shuuichi et al. | 435/158 |
| 6,030,820 A | * | 2/2000 | Morioka et al. | 435/158 |

FOREIGN PATENT DOCUMENTS

| EP | 0 136 805 A2 | 4/1985 |
|---|---|---|
| EP | 0 908 523 A2 | 4/1999 |
| EP | 0 922 757 A1 | 6/1999 |

* cited by examiner

*Primary Examiner*—Herbert J. Lilling
(74) *Attorney, Agent, or Firm*—Fitch, Even, Tabin & Flannery

(57) ABSTRACT

The present invention discloses a process for producing erythritol by fermentation using a polysaccharide negative erythritol producing strain and recovering erythritol crystals by direct crystallization from the unrefined micro-organism-free fermentation broth. Direct crystallization of erythritol is performed at dry substance higher than 80% w/w. Recovery of erythritol crystals is at least 85% and purity of erythritol crystals is at least 99% w/w.

9 Claims, No Drawings

PROCESS FOR PRODUCING AND RECOVERING ERYTHRITOL FROM CULTURE MEDIUM CONTAINING THE SAME

TECHNICAL FIELD

The present invention relates to a process for producing and recovering erythritol crystals, more specifically to a fermentative method of producing erythritol without at the same time producing higher viscous polysaccharides, which is advantageous for recovering erythritol crystals by direct crystallisation from the unrefined microorganism-free fermentation broth.

BACKGROUND OF THE INVENTION

Erythritol-producing yeasts which produce erythritol through fermentation include those belonging to the genera Moniliella, Trichonosporoides, or Trichonosporon, typically used species are *Moniliella tomentosa* var. *pollinis*, and *Trichonosporoides megachiliensis*.

A conventional process for isolating and recovering erythritol from a culture medium obtained by culturing one of the erythritol-producing yeasts in an aqueous medium comprises subjecting said culture medium to a pre-treatment such as biomass removal by filtration, decolorisation with the use of active carbon, desalting and decolorizing the culture medium with ion exchange resins and then concentrating and cooling the same thereby crystallising the aimed erythritol.

Impurities, which affect isolation, crystallisation and/or recovery of erythritol, comprise the following constituents:

Polyols such as glycerol and ribitol

Oligosaccharides, including disaccharides and higher ones contained in the starting starch hydrolysate as well as reaction products formed therefrom.

Viscous microbial polysaccharides produced by the yeast.

Due to the formation of the polysaccharides the viscosity of the medium increases. This results in a decreased oxygen transfer rate and by anaerobic fermentation part of the carbohydrate source is converted into ethanol, thereby reducing the production of erythritol. Furthermore highly viscous fermentation broths give problems in filtering-off the cells and polyol recovery is very difficult.

EP 0 327 016 describes a process for recovering highly pure erythritol from an erythritol-containing culture medium, by passing the microorganism-free fermentation broth through chromatographic separation columns packed with alkali metal or ammonium type strongly acidic cation exchange resins. Removal of various salts, colouring material, various oligosaccharides and polysaccharides is obtained. The process comprises culturing an erythritol producing microorganism in an aqueous medium under aerobic conditions; removing the cells from the resulting culture medium; passing the obtained supernatant through separation columns packed with alkali metal or ammonium type strongly acidic cation exchange resins; eluting the same with water; collecting fractions containing erythritol as the main component therefrom; and then recovering erythritol from these fractions. This process requires very high consumption of water and the separated components are very diluted, resulting in high evaporation costs. Furthermore the investment cost of such separation equipment is high.

EP 0 908 523 relates to a process for producing high-purity erythritol crystals. The process comprises a crystallisation step and a crystal separating step wherein an erythritol concentration of the erythritol-containing aqueous solution is adjusted to 30–60% by weight at the beginning of the crystallisation step. Prior to the crystallisation step the process comprises a microbe-separating step, and a chromatographic separation.

Derwent Abstract of Japanese patent JP 10287603 describes the acidic treatment of the microorganism-free erythritol containing fermentation broth for hydrolysing the formed polysaccharides and impurities. The hydrolysis converts certain impurities into other less viscous by-products but in principle the overall purity is not increased. These by-products are subsequently removed by conventional separation methods such as activated carbon and ion exchange treatment.

Derwent Abstract of Japanese patent JP 01215293 describes the recovery of erythritol from a polysaccharide containing fermentation broth with ultrafiltration membranes. Polysaccharides, which make the microorganism-free fermentation broth turbid, are completely removed by the ultrafiltration with membranes with a cut-off of 1,000 to 100,000 daltons and erythritol is recovered from the purified medium.

U.S. Pat. No. 4,906,569 relates to a process for isolating and recovering highly pure erythritol at a high crystallisation yield from a culture medium of an erythritol-producing micro-organism, which comprises separating and removing various impurities and by-products such as various salts, colouring materials and polysaccharides. The impurities and by-products are removed through chromatographic separation with the use of a strongly acidic cation exchange resin.

All above cited references require in one way or another a purification step for removing formed polysaccharides, such as treatment with ion exchange resins, column chromatography, acid hydrolysis or ultrafiltration.

EP 0136805 describes a fermentation process in presence of high spore-forming colonies of the yeast-like fungus *Moniliella tomentosa* var. *pollinis*, resulting in 2.3–3.5% polysaccharides based on erythritol content. In presence of low spore-forming colonies up to 16–25% polysaccharides based on erythritol content are formed. Although with high spore-forming colonies the amount of polysaccharides is already reduced to 2.3–3.5% based on erythritol content, it is described that the culture broth is refined prior to concentration to 60% and to 80% dry substance. Erythritol is crystallised therefrom. Furthermore, long fermentation times up to 13 days are required to reach an erythritol yield of 34%.

Accordingly a need exist for a process for producing erythritol by fermentation and recovering erythritol crystals without purifying the micro-organism free fermentation culture medium. The recovery process should be free from 1) extensive refining, 2) generating big waste-streams, 3) high-energy demands, but should give a good recovery of highly pure erythritol crystals.

The current invention provides such a process.

SUMMARY OF THE INVENTION

The present invention discloses a process for producing erythritol by fermentation using micro-organisms and recovering erythritol crystals characterised in that said process is comprising the following steps:

a) taking as micro-organisms a polysaccharide negative erythritol producing strain which is producing less than 1% polysaccharides, preferably less than 0.1% polysaccharides based on erythritol content, b) preparing a fermentation culture medium, c) adding the micro-organisms to the fermentation culture medium, d) allowing the micro-organisms to grow until at least 50 g/L erythritol is obtained in the fermentation medium, e) removing the micro-organisms from the fermentation culture medium, f) concentrating the unrefined micro-organism-free fermentation culture medium to dry substance higher than 80% w/w, g) crystallising of erythritol, and h) collecting erythritol crystals.

The present invention relates to a process wherein the unrefined micro-organism fermentation culture medium is concentrated to a dry substance of at least 85% w/w, more preferably higher than 90% w/w.

The present invention further discloses a process wherein the erythritol crystals are collected with a recovery of at least 85%.

The present invention relates to a process wherein the erythritol crystals have a purity of at least 98% w/w, preferably 99% w/w.

The present invention relates to a process wherein the micro-organism is allowed to growth in less than 10 days.

The present invention relates to a process wherein the fermentation culture medium is prepared in a bubbled column reactor or airlift.

The current invention further discloses a process wherein in step a) *Moniliella tomentosa* var *pollinis* TCV324 is used.

Furthermore, the present invention relates to a polysaccharide negative erythritol producing Moniliella strain producing less than 1% polysaccharides, preferably less than 0.1% polysaccharides based on erythritol content. The present invention further relates to a polysaccharide negative erythritol producing Moniliella strain which is a *Moniliella tomentosa* strain, preferably *Moniliella tomentosa* var *pollinis* TCV324 deposited under the Budapest Treaty at BCCM/MUCL (Belgian Coordinated Collections of Micro-organisms/Mycothèque de l'Université Catholique de Louvain by Eridania Béghin Say, Vilvoorde R&D Centre, Havenstraat 84, B-1800 Vilvoorde) on Mar. 28, 1997 under number MUCL40385.

DETAILED DESCRIPTION OF THE INVENTION

The present invention discloses a process for producing erythritol by fermentation using micro-organisms and recovering erythritol crystals characterised in that said process is comprising the following steps:

a) taking as micro-organisms a polysaccharide negative erythritol producing strain which is producing less than 1% polysaccharides, preferably less than 0.1% polysaccharides based on erythritol content, b) preparing a fermentation culture medium, c) adding the micro-organisms to the fermentation culture medium, d) allowing the micro-organisms to grow until at least 50 g/L erythritol, preferably more than 100 g/L erythritol is obtained in the fermentation medium, e) removing the micro-organisms from the fermentation culture medium, f) concentrating the unrefined micro-organism-free fermentation culture medium to dry substance higher than 80% w/w, g) crystallising of erythritol, and h) collecting erythritol crystals.

Normally due to presence of considerable quantities of polysaccharides concentrating the unrefined micro-organism-free fermentation culture medium before crystallisation, results in a rapid increasing viscosity of the medium. As a result, the crystallisation rate is considerably lowered and it is very difficult to obtain highly pure crystals, since separation of crystalline mass from the mother liquor is very tedious.

The presence of more than 2% polysaccharides based on erythritol content is even too high to allow direct concentration to a dry substance higher than 80%.

Furthermore, these polysaccharides are precipitated during crystallisation of erythritol and the thus obtained erythritol crystals are contaminated with the polysaccharides. Re-dissolution of these impure crystals gives turbid solutions. It is therefore unavoidable to concentrate the culture medium only to a limited extent, thus preventing precipitation of polysaccharides, but which significantly lowers the crystallisation yield of erythritol. Crystallisation yield of erythritol is a function of dry substance. Too low dry substance results in a low crystal yield and recycling of the highly viscous mother liquor is excluded due to presence of polysaccharides.

The polysaccharide negative erythritol producing strain is selected from the genera Moniliella, Trichonosporoides and Trichonosporon.

The polysaccharide negative erythritol producing strain is producing less than 1% polysaccharides preferably less than 0.1% polysaccharides based on erythritol content. In presence of the wild type strain (CBS 461.67) 10.5 g/L polysaccharides or 33% polysaccharides based on erythritol content are collected.

The content of polysaccharides is determined by high performance liquid chromatography (cation exchange resin Shodex KC-811 $H^+$-form, eluted with 0.01% sulphuric acid solution and measuring area percent of the eluted peaks). Since the polysaccharide fraction is co-eluting with salts, and xanthan gum, which are added to the culture medium, the actual content of formed polysaccharides is determined by subtracting the zero-level (=background of salts and xanthan gum measured at starting point of fermentation) from the final level measured at the end of the fermentation, i.e. after removal of the biomass.

Raw materials used for preparing the fermentation culture medium are starch hydrolysate, containing more than 90% glucose as carbon source, and corn steep liquor, yeast extract and/or ammonium sulphate as nitrogen source. Xanthan gum and/or silicone oil can be added to suppress foaming.

The present invention relates to a process wherein the unrefined micro-organism fermentation culture medium is concentrated to a dry substance of at least 85% w/w, more preferably higher than 90% w/w and the collected erythritol crystals have a purity of at least 98% w/w, preferably 99% w/w.

The unrefined micro-organism-free culture medium is directly concentrated above 80% w/w dry substance, preferably to a dry substance of at least 85% w/w, more preferably above 90% w/w and by slowly cooling down to 20° C., erythritol crystals with 98–99% w/w purity are obtained. The direct crystallisation at high dry substance results in a high crystal yield, while the mother liquor can be recycled to the front of the crystalliser, due to the absence of polysaccharides. The unrefined micro-organism-free fermentation broth substantially free from polysaccharides is not suffering from increasing viscosity during concentration to high dry substance and the presence of glycerol, which can be a by-product of the fermentation, can favour the concentration to such high dry substance above 90%.

Prior to concentration and crystallisation, the biomass (micro-organisms) is removed by common known filtration techniques, such as centrifugation, pre-coated vacuum filtration or microfiltration. The resulting micro-organism-free fermentation broth is used as such for concentration and crystallisation of erythritol crystals. A refining step for removing residual impurities such as treatment with active carbon or with ion exchange resins is not included in the process.

The present invention relates to a process wherein the micro-organism is allowed to growth in less than 10 days and yet high erythritol concentrations are obtained.

The present invention relates to a process wherein the fermentation culture medium is prepared in a bubbled column reactor or airlift. The culture medium is not viscous and the fermentation for producing erythritol can be performed in such a simple fermentation reactor with low energy input.

Typically, the process of the current invention is performed under aerobic conditions with a strain selected from the genera Moniliella, Trichonosporoides and Trichonosporon. Preferably, mutant strains of *Moniliella tomentosa* var. *pollinis*, and *Trichonosporoides megachiliensis* are applied, more preferably the mutant strain *Moniliella tomentosa* var. *pollinis* TCV324. The mutant strains can be obtained by classic mutagenesis such as UV irradiation, nitrous acid, ethyl methane sulphonate (EMS), diethyl sulphate, N-methyl-N'-nitrosoguanidine (NTG) treatment, acridine treatment and the like. Polysaccharide negative erythritol producing strains which are producing less than 1% polysaccharides based on erythritol content, are preferably obtained by mutagenesis in presence of N-methyl-N'-nitrosoguanidine (NTG). The isolated colonies are cultivated for 5 days and the cell-free supernatant is mixed with isopropanol and the formed precipitate is dried and weighted. The colonies, which are giving the lowest amount of precipitate, are selected.

The fermentation with *Moniliella tomentosa* var. *pollinis* TCV 364 results in a polysaccharide content lower than 1 g/L or less than 1% polysaccharides preferably less than 0.1% polysaccharides based on erythritol content.

The present invention relates to a polysaccharide negative erythritol producing Moniliella strain producing less than 1% polysaccharides, preferably less than 0.1% polysaccharides based on erythritol content.

The present invention further relates to a polysaccharide negative erythritol producing Moniliella strain which is a *Moniliella tomentosa* strain, preferably *Moniliella tomentosa* var *pollinis* TCV324 deposited under the Budapest Treaty at BCCM/MUCL (Belgian Coordinated Collections of Micro-organisms/Mycothèque de l'Université Catholique de Louvain by Eridania Béghin Say, Vilvoorde R&D Centre, Havenstraat 84, B-1800 Vilvoorde) on Mar. 28, 1997 under number MUCL40385.

The absence of polysaccharides gives substantial advantages for the fermentation, for the removal of micro-organisms, and for the crystallisation:

1. The culture medium is not viscous and the fermentation for producing erythritol can be performed in a simple fermentation reactor with low energy input, such as an airlift or a bubble column reactor, preferably in a bubbled column reactor.
2. The applied mutant strain is very stable towards reversion.
3. Due to the lower viscosity, a better oxygen transfer is obtained, resulting in a lower ethanol production and increased erythritol yield. Erythritol concentrations higher than 250 g/L or 300 g/L can be reached. These high erythritol concentrations are obtained in less than 10 days fermentation time.
4. The absence of polysaccharides formed allows a better diffusion in the cells whereby the fermentation can be performed in presence of higher concentrations of the nitrogen source, which also reduces the fermentation time considerably.
5. The lower viscosity results in an improved and faster biomass filtration and the unrefined micro-organism-free fermentation broth is directly subjected to concentration to high dry substance, crystallisation and collection of erythritol crystals, without pre-treatment of active carbon and ion exchange resin.
6. The unrefined micro-organism-free fermentation broth is directly concentrated above 80% w/w dry substance and gives high crystal yield of erythritol.
7. High erythritol recovery, of at least 85% is obtained and less diluted waste stream is produced.
8. Erythritol crystals with 98–99% w/w purity are obtained.

The obtained erythritol crystals can be dried according to conventional methods e.g. with a fluidised bed-type dryer.

To increase the purity above 99.5% w/w, the erythritol crystals, which are 98–99% w/w pure (determined by high performance liquid chromatography (cation exchange resin Shodex KC-811 H$^+$-form, eluted with 0.01% sulphuric acid solution and measuring area percent of the eluted peaks) can be re-dissolved, decolourised and desalted by means of active carbon and/or ion exchange resins, prior to a second concentration and crystallisation. The mother liquor can be recycled to the first crystallisation step.

The present invention is illustrated by way of the following examples.

Example 1 describes a mutagenesis method for obtaining the mutant strain *Moniliella tomentosa* var. *pollinis* TCV 364.

Example 2 describes the inoculation and fermentation with the native strain CBS 461.67, and the yield of erythritol and content of polysaccharides are compared to the fermentation with the mutant strain *Moniliella tomentosa* var. *pollinis* TCV 364 (example 4).

Example 3 describes the inoculation and fermentation with the high spore-forming substrain described in EP 0136805, and the viscosity of the micro-organism free fermentation broth is compared to the viscosity of the micro-organism fermentation broth obtained with the mutant strain *Moniliella tomentosa* var. *pollinis* TCV 364 (example 4). The viscosity of the fermentation broth increases with the content of polysaccharides present in the fermentation broth.

Example 5 describes the fermentation with *Moniliella tomentosa* var. *pollinis* TCV 364 on pilot scale, followed by the recovery of erythritol crystals (=downstream processing).

EXAMPLE 1

Mutagenesis to Obtain *Moniliella tomentosa* var. *pollinis* TCV 364

*Moniliella pollinis* was cultivated at 30° C. in shake-flasks on a medium containing 30% glucose and 1% yeast extract. After 2 days 1 ml of a saturated N-methyl-N'-nitrosoguanidine (NTG) solution was added to the culture and incubated for 1 hr under agitation. The cells were centrifuged and washed 2 times with fresh culture medium. The cells were diluted in sterile water and plated on solid medium containing 20% glucose, 1% yeast extract and 2% agar and incubated at 30° C. for one week. Isolated colonies were cultivated in liquid medium for 5 days. The cells were separated by centrifigation and the cell-free supernatant was mixed with 2 parts of isopropanol. The precipitate was dried and weighted. Colonies giving the lowest amount of precipitate were selected.

COMPARATIVE EXAMPLE 2

Polysaccharide Formation—Native Strain CBS 461.67

1. Inoculation—Erlenmeyer

Crystalline dextrose (C☆Dex02001) was dissolved in 50 ml water until a concentration of 30% w/v was reached. Yeast extract (Ohly) 1% w/v was added. The medium was inoculated with a few colonies of the petri dish. The temperature was 30° C. and the total medium was shaken for 3 days at 100 shakes/min.

2. Fermentation

The total working-volume was 1.2 L and crystalline dextrose (C☆Dex02001) was added to water until a concentration of 30% w/v was reached. 5% w/v corn steep liquor (C☆Plus15855, 5%), which was sterilised separately in 200 ml water, was added followed by the inoculum which was prepared in the Erlenmeyer, and 500 ppm silicone oil (SAG) and 500 ppm Xanthan. The temperature was 35° C., and the broth was stirred at 600–1000 rpm. The total fermentation time was 120 h. Content of polysaccharides and erythritol were determined by HPLC and the results are displayed in table 1.

COMPARATIVE EXAMPLE 3

Viscosity of Fermentation Broth with High-Spore Forming Substrain Described in EP 0136805

Inoculum was prepared by applying the same reaction conditions as described in example 2. Instead of using the native strain, colonies of the high spore forming substrain described in EP 0136805 were inoculated. Fermentation conditions were similar as described in example 2.

The viscosity of the micro-organism free fermentation broth was compared to the viscosity of the micro-organism free fermentation broth obtained with mutant strain *Moniliella tomentosa* var. *pollinis* TCV 364. The results are displayed in Table 2.

EXAMPLE 4

Polysaccharide Formation—Mutant Strain TCV 364

Inoculum was prepared by applying the same reaction conditions as described in example 2. Instead of using the native strain, colonies of the mutant strain *Moniliella tomentosa* var. *pollinis* TCV 364 were inoculated. Fermentation conditions were similar as described in example 2.

Content of polysaccharides and erythritol were determined by HPLC and the results are displayed in table 1.

TABLE 1

| | Wild strain CBS 461.67 | Mutant strain TCV 364 |
| --- | --- | --- |
| Polysaccharide g/L | 10.5 | 0.7 |
| Polysaccharide % on erythritol content | 33.0% | 1.0% |
| Erythritol g/L | 31.8 | 68.5 |
| Ethanol g/L | 26.0 | 22.0 |
| Ethanol % on erythritol content | 81.8% | 32.1% |

TABLE 2

| | High spore forming substrain described in EP 0136805 | Mutant strain TCV 364 |
| --- | --- | --- |
| Viscosity (at 64° C., in mPas/sec) of micro-organism-free fermentation broth concentrated to 64% dry substance | 34.1 | 25.5 |

EXAMPLE 5

Fermentation+Downstream Processing Fermentation

A 6000-L bubble column reactor was sterilised for 30 minutes at 121° C. Sterile water was added, and starch hydrolysate (C☆Plus02668, 95% dextrose, 70% d.s.) was added until the final concentration of dextrose after inoculation (as calculated on 3600 L) was between 220 and 250 g/L. The temperature of the broth was kept constant at 35° C. Sterile air was injected into the reactor to obtain a superficial gas velocity of between 5 and 15 cm/sec. The volume was inoculated with a 3-day-old pre-culture (of which the volume is between 500 L and 1000 L). 4.5% to 5% w/v Corn steep liquor (C☆Plus15855, 50% d.s.), 400 to 500 ppm silicone oil (SAG471), and 400 to 500 ppm Xanthan were sterilised during 30 minutes at 121° C. (concentrations were calculated on the final volume of 3600 L) and added to the fermentation broth. After further 30 to 40 hours the addition of pasteurized starch hydrolysate (C☆Plus02668, 95% dextrose, 70% d.s.) was started to keep the dextrose level between 20 and 100 g/L. This addition was continued until the final volume of the broth was 4800 L. Fermentation was continued until the dextrose level in the broth was below 2 g/L, i.e in less than 10 days.

Final concentration of erythritol was between 250 and 300 g/L. 0.42% polysaccharides (based on erythritol content) were formed.

Crystallisation

Biomass was removed from fermentation broth by filtration on a pre-coated rotary vacuum filter. The clarified fermentation broth was concentrated in a batch vacuum evaporator up to a total dry solids content of 90% w/w at 90° C. This clarified liquor was transferred to an agitated batch cooling crystalliser. Cooling proceeded linear from 90° C. to 20° C. over a time period of 6 hours. Erythritol crystals were recovered by batch centrifugation. Crystals were washed in the centrifuge with cold water, ratio water to crystals is 15/100. The erythritol recovery was 85% and purity of the crystals was 99.1% w/w.

What is claimed is:

1. A process for producing erythritol by fermentation using micro-organisms and recovering erythritol crystals which comprises:

a) selecting as, a microorganism, a polysaccharide negative erythritol producing strain which produces less than 1% polysacchrides based on erythritol content, b) preparing a fermentation culture medium, c) adding the microorganism to the fermentation culture medium, d) allowing the strained of microorganisms to grow until at least 50 g/L erythritol is obtained in the fermentation medium, e) removing the microorganism from the fermentation culture medium, f) concentrating the unrefined microogranism free fermentation culture medium to dry substance higher than 80% w/w, g) crystallizing erythritol, and h) collecting erythritol crystals.

2. A process according to claim 1, wherein unrefined microorganism fermentation culture medium is concentrated to a dry substance of at least 85% w/w.

3. A process according to claim 1 or 2, wherein the erythritol crystals are collected with a recovery of at least 85%.

4. A process according to claim 1 or 2, wherein the erythritol crystals have a purity of at least 98% w/w.

5. A process according to claim 1 or 2, wherein the microorganism growth is allowed for less than 10 days in (d).

6. A process according to claim 1 to 2, wherein the fermentation culture medium is prepared in a bubbled column reactor or airlift.

7. A process according to claim 1, wherein the microorganism is *Moniliella tomentosa* var *pollinis* TCV362.

8. A process according to claim 3, wherein the unrefined microorganism fermentatin culture medium is concentrated to a dry substance of at least 90 or w/w.

9. A process according to claim 3, wherein the erythritol crystals have a purity of at least 99% w/w.

\* \* \* \* \*

UNITED STATES PATENT AND TRADEMARK OFFICE
CERTIFICATE OF CORRECTION

PATENT NO. : 6,440,712 B2
DATED : August 27, 2002
INVENTOR(S) : De Troostembergh et al.

It is certified that error appears in the above-identified patent and that said Letters Patent is hereby corrected as shown below:

<u>Column 3,</u>
Lines 26 and 34, "TCV324" corrected to -- TCV364 --.

<u>Column 5,</u>
Lines 22 and 46, "TCV324" corrected to -- TCV364 --.

<u>Column 10,</u>
Line 8, "TCV362" corrected to -- TCV364 --.

Signed and Sealed this

Third Day of February, 2004

JON W. DUDAS
*Acting Director of the United States Patent and Trademark Office*